(12) United States Patent
Zheng et al.

(10) Patent No.: US 7,455,850 B2
(45) Date of Patent: Nov. 25, 2008

(54) TWO-PART COSMETIC PRODUCT

(75) Inventors: Tao Zheng, Nanuet, NY (US); Jason Rothouse, Ridgewood, NJ (US); Leona G. Fleissman, Ridgewood, NJ (US)

(73) Assignee: Avon Products. Inc., New York, NY (US)

( * ) Notice: Subject to any disclaimer, the term of this patent is extended or adjusted under 35 U.S.C. 154(b) by 0 days.

(21) Appl. No.: 11/020,612

(22) Filed: Dec. 23, 2004

(65) Prior Publication Data

US 2006/0140895 A1    Jun. 29, 2006

(51) Int. Cl.
*A61K 8/02* (2006.01)

(52) U.S. Cl. ..................................... 424/401
(58) Field of Classification Search .................. 424/401
See application file for complete search history.

(56) References Cited

U.S. PATENT DOCUMENTS

| | | | | |
|---|---|---|---|---|
| 5,688,831 A | | 11/1997 | El-Nokaly et al. .......... 514/938 |
| 6,010,686 A | * | 1/2000 | De La Poterie et al. ....... 424/64 |
| 6,045,783 A | | 4/2000 | Macchio et al. ............... 424/64 |
| 6,497,891 B2 | * | 12/2002 | Bara .......................... 424/401 |
| 2003/0049212 A1 | * | 3/2003 | Robinson et al. .............. 424/59 |
| 2005/0129641 A1 | * | 6/2005 | Arnaud et al. ................. 424/63 |

FOREIGN PATENT DOCUMENTS

| | | |
|---|---|---|
| EP | 0163696 | 12/1985 |
| EP | 0379409 | 7/1990 |
| EP | 0467767 | 1/1992 |
| EP | 0501523 A1 | 9/1992 |
| EP | 0501523 B1 | 9/1997 |

OTHER PUBLICATIONS

"Treated Pigments," Kobo Products, Inc., South Plainfield, New Jersey, May 2000.
"Sebum Control Using Powdered Silicone Elastomers," Dow Corning, 2000.

* cited by examiner

*Primary Examiner*—Sreeni Padmanabhan
*Assistant Examiner*—Renee Claytor
(74) *Attorney, Agent, or Firm*—Joan M. McGillycuddy; Charles S. Zeller; Anthony M. Santini

(57) ABSTRACT

There are provided two-part cosmetic products and methods for imparting a filling and swelling effect to skin, lips, hair, eyelashes, and/or eyebrows. The two-part cosmetic product has an anhydrous liquid or semi-solid first part composition with a water absorbent polymer, and a water-based second part composition with a water soluble or water dispersible film former. Optionally, the anhydrous first part composition has an oil absorbent polymer. Preferably, the product is wax-free, and is incorporated into a lip line filler, a volumizing mascara, and/or an anti-wrinkle skin care composition.

20 Claims, No Drawings

TWO-PART COSMETIC PRODUCT

BACKGROUND OF THE INVENTION

1. Field of the Invention

The present invention relates to methods for cosmetically improving the appearance of skin, lips, hair, eyelashes, and/or eyebrows. More particularly, the present invention relates to novel topical compositions that are useful to enhance the overall appearance of the skin, lips, hair, eyelashes, and/or eyebrows, by imparting a filling and/or swelling effect, and/or reducing the appearance of fine lines and wrinkles.

2. Description of the Related Art

For many cosmetic formulations, it is desirable to have certain parts of the skin, especially the face, to appear fuller. Facial lines and wrinkles can be present anywhere on the face, but are particularly noticeable, and occur most frequently, on the lips and around the lip area. The appearance of fine facial lines and wrinkles is a concern for many during the aging process. Reduction of, or at least concealing, the appearance of facial lines and/or wrinkles is an important function of cosmetic skin compositions.

Lip compositions are commonly used to impart a cosmetic finish or color to the lip. Conventional lip compositions are semisolid mixtures of waxes, oils, and colorants. Wearers of lipstick and other colored lip products have traditionally encountered difficulty with fine facial lines that commonly form around the lips. These facial lines often cause lipstick to bleed or spread into them. When bleeding occurs, the lipstick will settle into the lines and emphasize their existence by depositing color in the crevices. Use of colored lipliner to aid in the maintenance of lipstick on the lips can be somewhat effective, but it still does not fully prevent the bleeding. Traditional lipliner aims to prevent the bleeding of lipstick by forming a barrier around the lips. Many lipliners are in the form of a waxy pencil that deposit color on the lips in hopes of maximizing the length and the intensity of the lip color. However, lipliner can easily wear off and the lipstick can subsequently bleed into the facial lines. Conventional lipliners are not designed to take preventative measures with regard to fine lines and wrinkles on or surrounding the lips.

Another desirable attribute for cosmetic formulations is to provide volumizing effect to hair, eyelashes, and eyebrows. Mascara compositions are one type of product that is commonly used to achieve aesthetic effects such as thickening and/or lengthening of eyelashes or eyebrows by using glossy film formers, waxes, colorants, latexes, and/or thickening agents.

The present invention is a two-part composition for a cosmetic for application to skin surfaces, such as the facial lines on or around the lip area. The composition can also be used in formulations for application to the hair, eyelashes, and eyebrows.

It would be desirable to have cosmetic products that provide both filling and swelling effects to skin, lips, hair, eyelashes, and/or eyebrows. It would be further desirable to have cosmetic products that provide both a filling and swelling effect, and also exhibit excellent feel aesthetics.

SUMMARY OF THE INVENTION

It is an object of the present invention to provide two-part cosmetic products for imparting filling and swelling effects to skin, lips, hair, eyelashes, and/or eyebrows.

It is another object of the present invention to provide two-part cosmetic products for imparting filling and swelling effects and that exhibit excellent feel aesthetics.

It is still another object of the present invention to provide two-part cosmetic products for imparting filling and swelling effects, that are liquid or semi-solid in form.

It is a further object of the present invention to provide two-part cosmetic products for imparting filling and swelling effects that are wax-free.

It is yet a further object of the invention to provide a two-part cosmetic product in kit form having a first anhydrous composition and a second aqueous composition, the anhydrous and aqueous composition being applied sequentially to the skin, especially the lips, of the consumer.

According to these and other objects and advantages of the present invention, there are provided two-part cosmetic products for imparting a filling and swelling effect to skin, lips, hair, eyelashes, and/or eyebrows, and methods for applying same. The two-part cosmetic products of the present invention comprise a first part composition having an anhydrous component with a water absorbent polymer and an optional oil absorbent polymer, and a second part water-based composition optionally containing a water soluble or water dispersible film former. Preferably, the two-part cosmetic products of the present invention comprise the first part anhydrous composition having an anhydrous liquid or semi-solid component with a water absorbent polymer and an optional oil absorbent polymer. A preferred cosmetic product includes a wax-free lip line filler composition.

Further according to this and other objects and advantages of the present invention, there are also provided methods for imparting a filling and swelling effect to skin, lips, hair, eyelashes, and/or eyebrows. A method includes applying to the skin, lips, hair, eyelashes, and/or eyebrows a first part anhydrous composition having an anhydrous liquid or semi-solid component with a water absorbent polymer and optionally an oil absorbent polymer, and a water-based second part composition, preferably containing a water soluble or water dispersible film former. Preferably, the first part anhydrous composition is applied first to the skin, lips, hair, eyelashes, or eyebrows as a base coat, and then the second part or water-based composition is applied as a second or top coat.

In another aspect of the invention, the first part anhydrous composition having an anhydrous liquid or semi-solid component with a water absorbent polymer and an oil absorbent polymer, is applied to premoistened skin, especially lips, or is applied to such skin and is thereafter moistened. Preferably, the second part composition is used to pre- or post-moisten the skin or lips for uniformity of final result.

DETAILED DESCRIPTION OF THE INVENTION

The present invention provides cosmetic products that impart instant wrinkle and fine line filling and swelling effect to skin, lips, hair, eyelashes, and/or eyebrows. Further, it includes methods for imparting a filling or swelling effect to skin, lips, hair, eyelashes, and/or eyebrows by applying one of the compositions thereto.

The cosmetic products have two compositional parts for sequential application to skin, lips, hair, eyelashes, and/or eyebrows. The first part compositions are anhydrous and have an anhydrous component with at least one water absorbent polymer and at least one oil absorbent polymer. Preferably, the first part anhydrous composition is a base coat. The first part anhydrous composition can take any liquid or semi-solid composition form, such as a suspension or a dispersion. Preferably, the water absorbent polymer is present at about 0.1 wt % to about 50 wt % based on the total weight of the first part composition. More preferably, the water absorbent polymer is present at about 1 wt % to about 30 wt % based on the total weight of the first part composition. Most preferably, the water absorbent polymer is present at about 5 wt % to about 25 wt % based on the total weight of the first part composition.

Preferably, the oil absorbent polymer is present at about 0 wt % to about 25 wt % based on the total weight of the first part composition. More preferably, the oil absorbent polymer is present at about 0.01 wt % to about 10 wt % based on the total weight of the first part composition. Most preferably, the oil absorbent polymer is present at about 0.1 wt % to about 5 wt % based on the total weight of the first part composition. When the composition is for use on lips, preferably, the oil absorbent polymer is present at about 0.01 wt % to about 5 wt % based on the total weight of the first part composition. When the composition is for use on lips, more preferably, the oil absorbent polymer is present at about 0.01 wt % to about 1 wt % based on the total weight of the first part composition. When the composition is for use on lips, most preferably, the oil absorbent polymer is present at about 0.1 wt % to about 0.25 wt % based on the total weight of the first part composition. In a preferred embodiment, a first part composition of the present invention for use on lips has up to 0.1 wt % of oil absorbent polymer, based on the total weight of the first part composition.

The second part compositions also have a water-based composition component optionally containing at least one water soluble or water dispersible film former. Preferably, the water-based composition component is an activator coat or top coat. Preferably, water is present at about 40 wt % to about 99 wt % based on the total weight of the second part composition. More preferably, water is present at about 70 wt % to about 95 wt % based on the total weight of the second part composition. Most preferably, water is present at about 80 wt % to about 95 wt % based on the total weight of the second part composition.

Optionally, either the first part anhydrous composition or the water-based top coat or second part composition may have one or more optical blurring materials, also referred to as soft focus materials. These materials include, but are not limited to, polymethylmethacrylate, nylon, silica, cellulose, and vinyl dimethicone/methicone silsesquioxane crosspolymer. Preferably, the optical blurring, and/or light diffusing materials are present at about 0.01 wt % to about 20 wt %. More preferably, these materials are used at about 0.1 wt % to about 15 wt %. Most preferably, these materials are used at about 1 wt % to about 10%.

Water soluble or water dispersible film formers that can be used in the water-based top coat composition components of the present compositions include, but are not limited to, one or more acrylic polymers or co-polymers, PVP (polyvinylpyrrolidone), styrene polymers, starch, or any combinations thereof.

Water soluble or water dispersible film formers that can be used in the water-based top coat compositions of the present products also include, but are not limited to, butylated PVP (e.g. GANEX P-904, distributed by ISP), 2-butendoic acid (e.g. GANTREZ S-97-BF, distributed by ISP), diglycol/CHDM(cyclohexanedimethanol)/isopthalates/SIP (sulfoisophthalates) copolymer (e.g. AQ-55S, distributed by Eastman), acrylic copolymer emulsion (e.g. COVACRYL A15 and COVACRYL E14, distributed by LCW), acrylates/ammonium methacrylates copolymer in water (e.g. ULTRASOL 2000C, distributed by Presperse), modified starch (e.g. PURE COAT B793, distributed by Grain Processing), sulfonated poylstyrene (e.g. FLEXAN II, distributed by National Starch), acrylates/C12-22 alkylmethacrylate copolymer (e.g. ALLIANZ OPT, distributed by ISP), ethylene carboxamide/acrylomidomethyl propanesulfonic acid/methacrylic acid (e.g. ACUDYNE SCP, distributed by Rohm and Haas), acrylates/ethylhexyl acrylate copolymer (e.g. DAITASOL SJ, distributed by Daito Kasei Kogyo Co., Ltd.), or any combinations thereof. Preferred water soluble or water dispersible film formers are DAITASOL SJ, ACUDYNE SCP, ALLIANZ OPT, COVACRYL A15, COVACRYL E14, or any combinations thereof. The film former also provides gloss.

Preferably, the water soluble or water dispersible film former is present at about 0 wt % to about 30 wt % based on the total weight of the second part composition. More preferably, the water soluble or water dispersible film former is present at about 0.5 wt % to about 20 wt % based on the total weight of the second part composition. Most preferably, the water soluble or water dispersible film former is present at about 1 wt % to about 15 wt % based on the total weight of the second part composition. Preferably, the compositions are wax-free.

The first and second part compositions typically have a vehicle or carrier. The vehicle should be a physiologically acceptable or suitable vehicle. A "physiologically acceptable vehicle" or a "suitable vehicle" means any vehicle for a drug, cosmetic or medicament that is suitable for use in direct, safe contact with human tissues. The present composition is preferably incorporated into a suitable topical vehicle to form a topical formulation prior to applying. Preferably, each part of the present two-part cosmetic products has a suitable vehicle. The anhydrous compositions that can be used in the present cosmetic products are gel-based, silicone-based, solvent-based, powder-based, oil-based, or any combinations thereof. Preferably, the anhydrous first-part compositions have gel, silicone, oil, or solvent as a vehicle for the water absorbent polymer and the oil absorbent polymer. A representative gel is hydrocarbon gel, such as hydrogenated polyisobutene. A representative oil is polyglycerol diisostearate.

Cosmetic vehicles that can be used in the anhydrous or first part base coat compositions of the present products to disperse the water absorbent polymer include, but are not limited to, butylene glycol, propylene glycol, polyglycerol diisostearate, dimethylsiloxane/glycol copolymer, isopropyl myristate, triisostearyl citrate, or any combinations thereof.

In general, the water absorbent polymer can be dispersed in different esters. Suitable silicone compatible organic esters are mono-, di-, and triesters. The compositions may include one or more of these esters, or mixtures thereof.

Monoesters are defined as esters formed by the reaction of a monocarboxylic acid having the formula R—COOH, wherein R is a straight or branched chain saturated or unsaturated alkyl having 2 to about 30 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. In a preferred embodiment of the invention, the acid is an alpha hydroxy acid. Either one or both of the acid or alcohol may be a "fatty"-acid or alcohol, i.e. may have from about 6 to 22 carbon atoms. Examples of monoester oils that may be used in the present compositions include, but are not limited to, hexyldecyl benzoate, hexyl laurate, hexadecyl isostearate, hexydecyl laurate, hexyldecyl octanoate, hexyldecyl oleate, hexyldecyl palmitate, hexyldecyl stearate, hexyldodecyl salicylate, hexyl isostearate, butyl acetate, butyl isostearate, butyl oleate, butyl octyl oleate, cetyl palmitate, ceyl octanoate, cetyl laurate, cetyl lactate, isostearyl isononanoate, cetyl isononanoate, cetyl stearate, stearyl lactate, stearyl octanoate, stearyl heptanoate, stearyl stearate, or any combinations thereof. In the above nomenclature, the first term indicates the alcohol and the second term indicates the acid in the reaction.

For example, stearyl octanoate is the reaction product of stearyl alcohol and octanoic acid.

Suitable diesters that may be used in the present compositions are the reaction product of a dicarboxylic acid and an aliphatic or aromatic alcohol. The dicarboxylic acid may contain from 2 to about 30 carbon atoms, and may be in the straight or branched chain, saturated or unsaturated form. The dicarboxylic acid may be subsituted with one or more hydroxyl group. The aliphatic or aromatic alcohol may also contain 2 to about 30 carbon atoms, and may be in the straight or branched chain, saturated, or unsaturated form. The aliphatic or aromatic alcohol may be substituted with one or more substitutents such as hydroxyl. Preferably, one or more of the acid or alcohol is a fatty acid or alcohol, i.e. contains 14 to 22 carbon atoms. The dicarboxylic acid may also be an alpha hydroxy acid. Examples of diester oils that may be used in the present compositions include, but are not limited to, diisostearyl malate, neopentyl glycol dioctanoate, dibutyl sebacate, di-C.sub.12-13 alkyl malate, dicetearyl dimer dilinoleate, dicetyl adipate, diisocetyl adipate, diisononyl adipate, diisostearyl dimer dilinoleate, disostearyl fumarate, diisostearyl malate, or any combinations thereof.

Suitable triesters comprise the reaction product of a tricarboxylic acid and an aliphatic or aromatic alcohol. As with the mono- and diesters mentioned above, the acid and alcohol contain 2 to about 30 carbon atoms, and may be saturated or unsaturated, straight or branched chain, and may be substituted with one or more hydroxyl groups. Preferably, one or more of the acid or alcohol is a fatty acid or alcohol containing 14 to 22 carbon atoms. Examples of triesters that may be used in the present compositions include, but are not limited to, triarachidin, tributyl citrate, triisostearyl citrate, tri C12-13 alkyl citrate, tricaprylin, tricaprylyl citrate, tridecyl behenate, trioctyldodecyl citrate, tridecyl behenate, tridecyl cocoate, tridecyl isononanoate, or any combinations thereof.

A variety of cosmetic vehicles may be used in the anhydrous base coat compositions of the present products to disperse the oil absorbent polymer. Linear and cyclic volatile silicones are available from various commercial sources, including Dow Corning Corporation and General Electric. The Dow Corning volatile silicones are sold under the tradenames Dow Corning 244, 245, 344, and 200 fluids. These fluids include octamethylcyclotetrasiloxane, decamethylcyclopentasiloxane, hexamethyldisiloxane, or mixtures thereof.

Nonvolatile silicone oils, both water soluble and water insoluble, are also suitable for use as the non-volatile oil. Such silicones preferably have a viscosity ranging from about 10 to about 600,000 centistokes, preferably about 20 to about 100,000 centistokes at 25 degrees C. Suitable water insoluble silicones include amine functional silicones such as amodimethicone; phenyl substituted silicones such as bisphenylhexamethicone, phenyl trimethicone, or polyphenylmethylsiloxane; dimethicone; alkyl substituted dimethicones; or mixtures thereof.

The water absorbent polymers that can be used in the anhydrous compositions of the present cosmetic products include, but are not limited to, one or more crosslinked partially neutralized poly(acrylic acid), polyacrylamide, poly(ethylene oxide), poly(vinyl alcohol), sodium carboxymethylcellulose, sodium alginate, or any combinations thereof. To improve the water absorption process, a hydrophilic surfactant with a high hydrophilic-lypophilic balance ("HLB") value may be included in the anhydrous component. Preferably, the hydrophilic surfactant has an HLB value of at least 9.5. More preferably, the hydrophilic surfactant has an HLB value of at least 13.

Water absorbent polymers that can be used in the anhydrous first part compositions also include, but are not limited to, sodium acrylate (e.g. AQUA KEEP, distributed by Kobo Products, Inc.) and acrylamide/sodium acrylate copolymer (e.g. WATER LOCK G series and WATER LOCK A series, distributed by Grain Processing Corp.). The water absorbent polymer of the anhydrous first part composition provides for a swelling effect after absorption is triggered by the water-based second part composition.

The water absorbent polymers used in the anhydrous first part compositions are highly water absorbent and minimally will absorb 200% of their own weight. Preferably, the water absorbent polymers absorb and retain at least ten times their own weight in water, and most preferably retain at 20 or even more than 50 times their dry weight in water without dissolving in water. Such preferred polymers are sometimes referred to as "superabsorbent" polymers. A superabsorbent polymer holds water within molecular chains, yet retains the absorbed water even under pressure. This is different from a cotton or sponge, which absorb water by capillarity, but readily release the water when pressure is applied.

The absorption capability of a superabsorbent polymer relative to a particular material is determined by osmotic pressure and the polymer's affinity with that material, as well as the polymer's rubber elasticity. The lower the ion concentration of the surrounding water solution, the greater is the resultant difference in ion concentration, and the greater the resultant osmotic pressure. This osmotic pressure enables a superabsorbent polymer to absorb a large quantity of water. The rubber elasticity of a given polymer increases with the crosslinking density of that polymer. The absorption capacity of a given superabsorbent polymer reaches its maximum when its rubber elasticity attains equilibrium with its water absorbing power.

Superabsorbent polymers are crosslinked networks of flexible polymer chains. The most efficient water absorbers are polymer networks that carry dissociated, ionic functional groups. Whereas traditional absorbents, like cotton, take up liquids by a flow or convective mechanism, superabsorbents function by a diffusive mechanism.

Nonionic polymers absorb water by the energetic and entropic interactions made possible by mixing the aqueous fluids with the hydrophilic groups that are present along the polymer chain. The principal distinction of absorbent polymers over water-soluble polymers is the presence of crosslinks within the molecular structure of the absorbent polymers. The crosslinks connect the various polymer chains into a huge, insoluble molecule that nevertheless can change its shape and volume as it becomes solvated by water. The result of the absorption of solvent is a swollen, soft gel. Ionic absorbent polymers absorb more water than nonionic polymers, as a result of strong ion-dipole interactions.

The principal superabsorbent polymer preferably used is crosslinked, partially neutralized poly(acrylic acid), for example AQUA KEEP from Kobo Products Inc. Other polymers, like polyacrylamide, poly(ethylene oxide), poly(vinyl alcohol), sodium carboxymethylcellulose (CMC), and sodium alginate can also be used.

Another water absorbent polymer that can be used in the present products also includes, but is not limited to, WATER LOCK. WATER LOCK is the trade name for a family of superabsorbent polymers produced by Grain Processing Corporation of Muscatine, Iowa. By definition, a superabsorbent polymer must absorb a minimum of twenty times its own weight in water. WATER LOCK superabsorbent polymers far exceed that value. Moreover, the polymer must retain its original identity and have sufficient physical integrity to resist flow and fusion with neighboring particles, and to swell to equilibrium volume and not dissolve.

WATER LOCK superabsorbent polymers fall into two classifications:

Starch Graft Copolymers: Starch Graft Poly (2-propenamide-co-2-propenoic acid) available as the sodium or potassium salt; and Copolymer: Poly (2-propenamide-co-2-propenoic acid, sodium salt).

WATER LOCK superabsorbent polymers are off-white to tan in color, free-flowing powders, which absorb or immobilize large volumes of aqueous solutions at neutral or alkaline pH, including body fluids.

The oil absorbent polymers that can be used in the anhydrous compositions of the present products include, but are not limited to, one or more silicone elastomers, polyamides, or any combinations thereof. The oil absorbent polymer, such as a silicone elastomer (Dow Corning 9506 powder), provides elastic particles to fill wrinkle and fine lines on lips and/or skin instantly. A preferred oil absorbent polymer that can be used in the first part compositions is lauryl methacrylate/glycol dimethacrylate crosspolymer, for example, POLYTRAP 6603 Adsorber from AMCOL Health & Beauty Solutions, Inc./Cardinal Health. Other oil absorbent polymers that can be used in the present products also include, but are not limited to, isododecane/ethylene mixed copolymer (e.g. GEL BASE CODE 05895, from Brooks Industries Inc.), cyclomethicone blend (e.g. DOW CORNING 9040 SILICONE ELASTOMER BLEND, from Dow Corning), nylon 6-12 (e.g. ORGASOL 4000, from Atofina), and dimethicone/vinyl dimethicone crosspolymer (e.g. DOW CORNING 9506 COSMETIC POWDER, from Dow Corning).

An oil absorbent polymer used in the anhydrous compositions of the present products absorbs and retains at least 50% of its own weight in oil. To measure the oil absorption ability of different polymeric materials, an oil absorption test was performed. A "Fat Red" dye and squalene mixture (oil/artificial sebum) was prepared. To each 5 grams of squalene, 5 mg of Fat Red was added and thoroughly dissolved. Each polymer tested required about 4 grams of this mixture. The purpose of the Fat Red is to dye the squalene to better visualize the oil uptake in the sample. First, a plastic Petri dish was tared. A small pile of polymer to be tested, about 15 mm in diameter and 5 to 10 mm in height, was placed with a spatula in the center of the dish. The weight was recorded as the sample amount. With a transfer pipette, 4 grams of the Fat Red/squalene mixture was added around the sample pile, while taking care not to disturb the powder. The timer was started as the polymer powder took up the Fat Red. The time was noted when the pile was completely saturated. This was the initial uptake time. The Petri dish was covered and placed in a secure place for 24 hours. After 24 hours, the dish was uncovered and the excess squalene mixture was carefully removed from the Petri dish using the transfer pipette and Kimwipes. The polymer pile was not disturbed. Subsequently, the polymer pile and absorbed squalene were carefully transferred to a tared aluminum pan, and a new weight reading was taken. The percent "sebum" uptake can be determined by comparing the weight of the polymer before and after saturation by the Fat Red squalene mixture.

Thus, the present cosmetic products provide instant wrinkle filling by the oil absorbent polymer, as well as swelling effect by the water absorbent polymer. Furthermore, the present cosmetic products provide excellent feeling aesthetics from hydrocarbon gel and silicone elastomer.

Silicone elastomers have a skin feel unlike any of the silicone fluids. Their feel can be described as "smooth," "velvety" and "powdery," and their skin feel can be modified by controlling the amount of solvent in the formula, and therefore the degree of swelling. For silicone elastomers based on dimethicone polymers, the ideal solvent is cyclopentasiloxane (i.e., cyclomethicone pentamer, sometimes referred to as "D5"). Other solvents and organic oils swell these silicone elastomers to a much lesser extent, and this can be useful for modifying the esthetics and rheology of the silicone elastomer.

The shape of the elastomer particles also affects the skin feel of silicone elastomers. Silicone elastomers made by a suspension process are spherical particles. These spherical particles behave like small ball bearings when spread on the skin, providing a characteristic dry lubrication effect. This effect is diminished somewhat when the elastomer particles are swollen with solvent, presumably due to softening of the particles. Silicone elastomer gel particles made by the solvent process have irregular shapes because they are produced by a shearing process. Their irregular shape give these soft particles a distinctly different feel on the skin compared to the spherical particles produced by the suspension process.

It is preferred that the anhydrous first part composition, containing the water and oil absorbent polymers, is topically first applied as a base coat, followed by the application as a top coat of the second part water-based composition in a second step. However, the water-based composition may be topically applied first as a base coat, and the anhydrous component may be applied second as a top coat.

Colorants are any conventional colorant in any cosmetic composition that is used for the purpose of exhibiting color on skin, hair, or lips. Colorants that can be used in the anhydrous component of the present compositions include, but are not limited to, D&C Red No. 3, D&C Red No. 6, D&C Red No. 7, D&C Red No. 8, D&C Red No. 9, D&C Red No. 21, D&C Red 22, D&C Red No. 27, D&C Red 28, D&C Red No. 30, D&C Red No. 33, D&C Red 34, D&C Red No. 36, FD&C Red No. 40, D&C Yellow No. 5, FD&C Yellow No. 5, FD&C Yellow No. 6, D&C Yellow No. 10, D&C Green No. 3, D&C Green No. 5, D&C Orange No. 5, FD&C Blue No. 1, annatto, copper powder, bismuth oxychloride, guanine, bronze powder, iron oxides, carmel, manganese violet, carmine, mica, titanium dioxide-coated mica, carotene, titanium dioxide, chlorophyllin-calcium complex, zinc oxide, or any combinations thereof. Also suitable are chemically treated pigments such as isopropyl titanium triisostearate (ITT) (e.g. titanate from Kobo Products, Inc.), magnesium myristate, triethoxy caprylylsilane (e.g. silane from Kobo Products, Inc.), silicone (including methicone and dimethicone), C9-15 fluoroalcohol phosphates (e.g. perfluoroalcohol phosphate from Kobo Products, Inc.), acrylates/dimethicone copolymer (e.g. acrylic silicone copolymer (ASC) from Kobo Products, Inc.), C9-15 fluoroalcohol phosphates (methicone and alumina) (e.g. PF-Si hybrid (perfluoroalcohol phosphate-silicone treatment) from Kobo Products, Inc.), C9-15 fluoroalcohol phosphates (acrylates/dimethicone copolymer) (e.g. PF-ASC hybrid (perfluoroalcohol phosphate-acryl silicone copolymer) from Kobo Products, Inc.), lecithin, carnauba wax, polyethylene, chitosan, and lauroyl-lysine. Such chemically treated pigments are known to those of ordinary skill in the art and/or are listed in Kobo Products, Inc.'s Treated Pigments brochure (May 2000).

The cosmetic products of the present invention may have other ingredients such as one or more anesthetics, anti-allergenics, antifungals, anti-inflammatories, antimicrobials, antiseptics, chelating agents, emollients, emulsifiers, fragrances, humectants, lubricants, masking agents, medicaments, moisturizers, pH adjusters, preservatives, protectants, soothing agents, stabilizers, sunscreens, surfactants, thickeners, viscosity control agents, vitamins, pigments, bioactives such as those providing lip plumping or anti-wrinkle effect (e.g. vitamin A and derivatives thereof), or any combinations thereof. Such ingredients are known to those of ordinary skill in the art and/or are listed in the INCI Handbook and Dictionary, 10$^{th}$ Edition, Volume 4 (2004). Generally, these adjuvants and excipients will be incorporated in the first or second part compositions depending on whether they will are hydrophilic or lipophilic.

The cosmetic products can take any semisolid or liquid product form suitable for application to the skin, lips, hair, eyelashes, and/or eyebrows, such as a cream, ointment, solution, paste, pomade, gel, lotion, or mascara. Preferred products are lip line fillers, volumizing mascaras, and anti-wrinkle skin-care products. More preferable cosmetic products are wax-free lip line fillers.

The cosmetic products of the present invention may be provided in the form of a kit comprising the first part composition, the second part composition, optional other compositional components of the kit, and instructions for the use of the product. Additionally, the kit may include a holder or container for each of the compositional components of the kit.

The cosmetic products of the present invention may also be provided as a one-part anhydrous lip composition, in which the anhydrous composition is applied first, and the lips are then post-moistened, for example, with saliva.

The following are examples of products of the present invention and are not to be construed as limiting. Unless otherwise indicated, all percentages and parts are by weight. All ingredients are "as is" unless otherwise noted.

The following formulations were prepared. The ingredients were as set forth in Examples 1 to 3 below:

EXAMPLE 1

Lip Line Filler Anhydrous Base Coat

| Ingredient | Concentration |
|---|---|
| Polyglycerol Diisostearate | 25.8% |
| Corn Starch/Acrylamide/Sodium Acrylate Copolymer[1] | 23.4% |
| Hydrogenated Polycyclopentadiene[2] | 25.8% |
| DM Fluid 0.65 cst[3] | 17.56% |
| Silicone Resin -DimethylMethyl[4] | 2.44% |
| TiO2 | 2.38% |
| Cosmetic Red Iron Oxide | 1.33% |
| Black Iron Oxide | 0.63% |
| D&C Red 7 Calcium Lake | 0.66% |
|  | 100.00% |

[1]Grain Processing WATER LOCK A-180
[2]Kobo-Koboguard 5400 IDD (70% active)
[3]Dow Corning 200 Fluid 0.65 cst
[4]Dow Corning 9506 Elastomer Powder A premix of the first three ingredients was prepared and roller-milled. The silicone materials were premixed and the pigments added to that premix. The two premixes are then combined with mixing.

EXAMPLE 2

Foundation Anhydrous Base Coat

| Ingredient | Concentration |
|---|---|
| Dimethylsiloxane/Glycol Copolymer[1] | 29.13% |
| Polyglycerol Diisostearte[2] | 29.13% |
| Corn Starch/Acrylamide/Sodium Acrylate Copolyme[3] | 14.56% |
| Cyclopentasiloxane/DM Crosspolymer and DM/Vinyl DM Crosspolymer and Dimethiconol[4] | 9.71% |
| Phenyl Trimethicone/Organopoylsiloxane[5] | 9.71% |
| TiO2 PMMA Trtd | 3.13% |
| Red Iron Oxide PMMA Trtd | 0.11% |
| Black Iron Oxide PMMA Trtd | 0.10% |
| Yellow Ox PMMA Trtd | 0.50% |
| Bismuth Oxychloride | 1.01% |
| Polyethylene[6] | 2.91% |
|  | 100.00% |

[1]Dow Corning 193 Fluid
[2]Cognis-Lameform TGI
[3]Grain Processing WATER LOCK A-180
[4]Dow Corning 9546 Elastomer
[5]Grant Industries GRANSIL PM Gel
[6]Jeen Chemicals JEENATE 3H A premix of the first three ingredients was prepared and roller-milled. The next two materials were added individually with mixing to the premix, and a premix of the pigments was then added. Lastly, a melt of the polyethylene was added to form the complete composition.

EXAMPLE 3

Water-Based Top Coat

| Ingredient | Concentration |
|---|---|
| DI Water | 87.94% |
| Carbopol 940[1] | 0.37% |
| TEA 99% | 0.10% |
| Butylene Glycol | 3.06% |
| Covacryl E14[2] | 5.00% |
| Germall II[3] | 0.18% |
| Polyglycerol Diisostearate | 3.35% |
|  | 100.00% |

[1]Noveon
[2]LCW (30% active)
[3]Sutton Labs

The Carbopol is added to the water with vigorous mixing, and the solution neutralized with TEA. The remaining ingredients are added individually with mixing.

The first part base coat composition of Examples 1 or 2 was applied to the lips, and the second part top coat composition of Example 3 was thereafter applied to the lips. Upon application of the water-based top coat, the anhydrous base coat's water-absorbent polymer swelled and created a smoothed gelled coating on the surface of the lips. This imparted a filling and swelling effect to the lips, thereby reducing the appearance of fine lines and wrinkles.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method for imparting a filling and swelling effect to lips, comprising:
   first topically applying to the lips an anhydrous, wax-free liquid or semi-solid composition comprising a water absorbent polymer, wherein said water absorbent polymer is present at about 0.1 wt % to about 50 wt % based on the total weight of the composition and
   applying a wax-free, water-based composition comprising (i) from about 40% to about 99% by weight water and (ii) a water soluble or water dispersible film former onto said base coat as a top coat, wherein said water-based composition triggers absorption of water by said water absorbent polymer to thereby impart a filling and swelling effect to the lips which reduces the appearance of fine lines and wrinkles.

2. The method of claim 1, wherein said anhydrous composition is a liquid or semi-solid.

3. The method of claim 1, wherein said anhydrous composition further comprises an oil absorbent polymer present at about 0 wt % to about 25 wt %, based on the total weight of said anhydrous composition.

4. The method of claim 3, wherein said oil absorbent polymer is selected from the group consisting of silicone elastomer, polyamide, lauryl methacrylate/glycol dimethacrylate crosspolymer, and combinations thereof.

5. The method of claim 1, wherein said water-based composition further comprises water present at about 70 wt % to about 95 wt % based on the total weight of said water-based composition.

6. The method of claim 1, wherein said water-based composition has a hydrophilic surfactant with an HLB value of at least 9.5.

7. The method of claim 1, wherein said film former is selected from the group consisting of acrylic polymer or co-polymer, PVP, styrene polymer, starch, butylated PVP, 2-butendoic acid, diglycol/CHDM/isopthalate/SIP copolymer, acrylic copolymer emulsion, acrylate/ammonium methacrylate copolymer in water, modified starch, sulfonated polystyrene, acrylate/C12-22 alkylmethacrylate copolymer, ethylene carboxamide/acrylomidomethyl propanesulfonic acid/methacrylic acid, acrylate/ethylhexyl acrylate copolymer, and any combinations thereof.

8. The method of claim 1, wherein said anhydrous composition further comprises a vehicle selected from the group consisting of gel, silicone oil, solvent, butylene glycol, propylene glycol, polyglycerol diisostearate, dimethylsiloxane/glycol copolymer, isopropyl myristate, triisostearoyl citrate, and any combinations thereof.

9. The method of claim 1, wherein said anhydrous composition further comprises an optical blurring material.

10. The method of claim 1, wherein said anhydrous composition further comprises a colorant selected from the group consisting of D&C Red No. 3, D&C Red No. 6, D&C Red No. 7, D&C Red No. 8, D&C Red No. 9, D&C Red No. 21, D&C Red No. 22, D&C Red No. 27, D&C Red No. 28, D&C Red No. 30, D&C Red No. 33, D&C Red No. 34, D&C Red No. 36, FD&C Red No. 40, D&C Yellow No. 5, FD&C Yellow No. 5, FD&C Yellow No. 6, D&C Yellow No. 10, D&C Green No. 3, D&C Green No. 5, D&C Orange No. 5, FD&C Blue No. 1, annatto, copper powder, bismuth oxychloride, guanine, bronze powder, iron oxide, carmel, manganese violet, carmine, mica, titanium dioxide-coated mica, carotene, titanium dioxide, chlorophyllin-calcium complex, zinc oxide, and any combinations thereof.

11. A method for imparting a filling and swelling effect to lips, comprising:
   applying a wax-free water-based composition comprising (i) from about 40% to about 99% by weight water and (ii) a water soluble or water dispersible film former onto the lips as a base coat; and
   applying an anhydrous, wax-free composition comprising a water absorbent polymer onto the base coat, wherein said water absorbent polymer is present at about 0.1 wt % to about 50 wt % based on the total weight of the composition, wherein said water-based composition triggers absorption of water by said water absorbent polymer to thereby impart a filling and swelling effect to the lips which reduces the appearance of fine lines and wrinkles.

12. The method of claim 11, wherein said anhydrous composition is a liquid or semi-solid.

13. The method of claim 11, wherein said anhydrous composition further comprises an oil absorbent polymer present at about 0 wt % to about 25 wt %, based on the total weight of said anhydrous composition.

14. The method of claim 13, wherein said oil absorbent polymer is selected from the group consisting of silicone elastomer, polyamide, lauryl methacrylate/glycol dimethacrylate crosspolymer, and combinations thereof.

15. The method of claim 11, wherein said water-based composition further comprises water present at about 40 wt % to about 99 wt % based on the total weight of said water-based composition.

16. The method of claim 11, wherein said water-based composition has a hydrophilic surfactant with an HLB value of at least 9.5.

17. The method of claim 11, wherein said film former is selected from the group consisting of acrylic polymer or co-polymer, PVP, styrene polymer, starch, butylated PVP, 2-butendoic acid, diglycol/CHDM/isopthalate/SIP copolymer, acrylic copolymer emulsion, acrylate/ammonium methacrylate copolymer in water, modified starch, sulfonated polystyrene, acrylate/C12-22 alkylmethacrylate copolymer, ethylene carboxamide/acrylomidomethyl propanesulfonic acid/methacrylic acid, acrylate/ethylhexyl acrylate copolymer, and any combinations thereof.

18. The method of claim 11, wherein said anhydrous composition further comprises a vehicle selected from the group consisting of gel, silicone oil, solvent, butylene glycol, propylene glycol, polyglycerol diisostearate, dimethylsiloxane/glycol copolymer, isopropyl myristate, triisostearoyl citrate, and any combinations thereof.

19. The method of claim 11, wherein said anhydrous composition further comprises an optical blurring material.

20. The method of claim 11, wherein said anhydrous composition further comprises a colorant selected from the group consisting of D&C Red No. 3, D&C Red No. 6, D&C Red No. 7, D&C Red No. 8, D&C Red No. 9, D&C Red No. 21, D&C Red No. 22, D&C Red No. 27, D&C Red No. 28, D&C Red No. 30, D&C Red No. 33, D&C Red No. 34, D&C Red No. 36, FD&C Red No. 40, D&C Yellow No. 5, FD&C Yellow No. 5, FD&C Yellow No. 6, D&C Yellow No. 10, D&C Green No. 3, D&C Green No. 5, D&C Orange No. 5, FD&C Blue No. 1, annatto, copper powder, bismuth oxychloride, guanine, bronze powder, iron oxide, cannel, manganese violet, carmine, mica, titanium dioxide-coated mica, carotene, titanium dioxide, chiorophyllin-calcium complex, zinc oxide, and any combinations thereof.

* * * * *